United States Patent
Stolper et al.

(10) Patent No.: US 8,424,143 B2
(45) Date of Patent: Apr. 23, 2013

(54) ELECTRIC TOOTHBRUSH

(75) Inventors: Michael Stolper, Eschborn (DE); Heiko Bornheimer, Wiesbaden (DE); Joachim Lepper, Usingen (DE); Philipp Jung, Griesheim (DE); Armin Schwarz-Hartmann, Wendelsheim (DE); Peter Trawinski, Weiterstadt (DE)

(73) Assignee: Braun GmbH, Kronberg (DE)

( * ) Notice: Subject to any disclaimer, the term of this patent is extended or adjusted under 35 U.S.C. 154(b) by 203 days.

(21) Appl. No.: 12/971,383

(22) Filed: Dec. 17, 2010

(65) Prior Publication Data

US 2011/0138551 A1    Jun. 16, 2011

(30) Foreign Application Priority Data

Jun. 20, 2008   (EP) ..................... 08011214

(51) Int. Cl.
*A61C 17/22*    (2006.01)
(52) U.S. Cl.
USPC .............. 15/22.1; 318/55; 318/66; 318/68
(58) Field of Classification Search .............. 15/22.1; 310/68 R; 318/55, 66, 68
See application file for complete search history.

(56) References Cited

U.S. PATENT DOCUMENTS

| | | | | |
|---|---|---|---|---|
| 5,493,747 A | * | 2/1996 | Inakagata et al. | 15/22.1 |
| 5,561,881 A | * | 10/1996 | Klinger et al. | 15/22.1 |
| 6,140,802 A | * | 10/2000 | Lundell et al. | 320/136 |
| 6,989,649 B2 | * | 1/2006 | Mehlhorn | 318/806 |
| 7,696,728 B2 | * | 4/2010 | Cross et al. | 320/166 |
| 7,721,371 B2 | * | 5/2010 | Pfenniger et al. | 15/22.1 |
| 7,975,341 B2 | * | 7/2011 | Cai et al. | 15/22.1 |
| 8,032,964 B2 | * | 10/2011 | Farrell et al. | 15/22.1 |
| 2003/0000033 A1 | * | 1/2003 | Lev et al. | 15/28 |
| 2007/0273331 A1 | * | 11/2007 | Cross et al. | 320/115 |
| 2008/0196184 A1 | * | 8/2008 | Mary | 15/22.1 |

FOREIGN PATENT DOCUMENTS

| | | |
|---|---|---|
| DE | 2 99 12 009 U1 | 1/2000 |
| DE | 10 2005 063 045 A1 | 7/2007 |
| DE | 10 2006 004 146 A1 | 8/2007 |
| WO | WO 99/57672 A | 11/1999 |
| WO | WO 01/93776 A | 12/2001 |
| WO | WO 2008/053454 A | 5/2008 |

OTHER PUBLICATIONS

European Search Report dated Jan. 13, 2009.

\* cited by examiner

*Primary Examiner* — Monica Carter
*Assistant Examiner* — Michael Jennings
(74) *Attorney, Agent, or Firm* — John P. Colbert

(57) ABSTRACT

An electric toothbrush is disclosed. The toothbrush includes a housing; a brush; an electric motor for driving the brush; a power supply for providing the electric power required for operation of the toothbrush; a switch mechanism for turning the drive on and off; and an electronic circuit for adjusting the effective voltage ($U_{Mot}$) applied to the electric motor. In operation, a voltage supplied by the power supply declines with the discharge status of the power supply from a high-voltage range to a low-voltage range. During operation of the toothbrush in the high-voltage range (H), the effective voltage ($U_{Mot}$) applied to the electric motor is lowered to a level at which the electric motor has reached a rotational speed corresponding essentially to the rotational speed of the electric motor in the medium-voltage range.

9 Claims, 3 Drawing Sheets

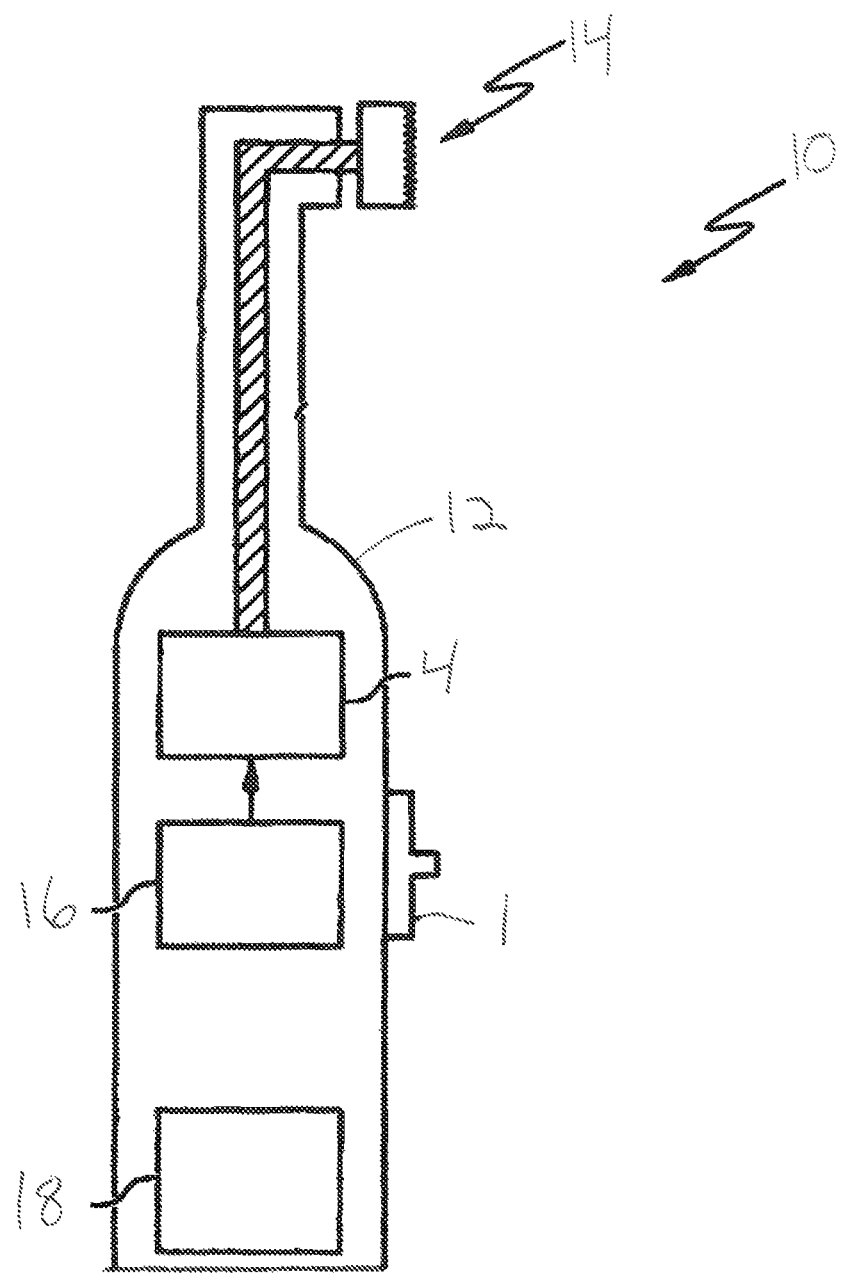

ELECTRIC TOOTHBRUSH

CROSS REFERENCE TO RELATED APPLICATIONS

This application claims the benefit of European Patent Convention Application No. 08011214.7, filed Jun. 20, 2008, the substance of which is incorporated by reference in its entirety herein.

FIELD OF THE INVENTION

The present disclosure relates to an electric toothbrush with a housing, a brush, a drive, for driving the brush, a power supply and a switch mechanism for turning the drive on and off by a user.

BACKGROUND OF THE INVENTION

DE 10 2006 004 146 A1 describes an electric toothbrush comprising a housing that functions as a handle and an electric motor that can move a bristle field carrier in the longitudinal direction of the housing as well as across its longitudinal direction with an oscillating action. The toothbrush is provided with a battery and a voltage stabilization circuit which supplies a stabilized power supply voltage to the electric motor.

DE 2 99 12 009 U1 describes an electric toothbrush having a drive with which the brush executes a rotating and reversing movement during tooth cleaning, whereby the rotational speed of the brush is either constant or is continuously variable.

DE 10 2005 063 045 A1 describes a discharge status display by means of which the almost discharged status of a battery can be recognized and displayed. The discharge status display comprises a display device designed as an LED, which lights up when the battery voltage drops below a certain threshold level.

With known battery-operated electric toothbrushes having a brush head that rotates with an oscillating action, the rotational speed of the drive motor changes with the voltage of the battery, i.e., when the battery is fully charged, the voltage and thus the rotational speed are much higher than when the battery has already supplied power for several tooth-brushing operations. The initially more rapid brushing movements of the bristles with new batteries because of the higher rotational speed are perceived as unpleasant in particular by users who have previously been using a manual toothbrush.

There thus exists a need for an electric toothbrush, which can be manufactured inexpensively and which is characterized by an operating performance that is perceived by the user as not requiring much adjustment.

SUMMARY OF THE INVENTION

In one embodiment, an electric toothbrush is provided. The toothbrush includes a housing; a brush; an electric motor for driving the brush; a power supply for providing the electric power required for operation of the toothbrush; a switch mechanism for turning the drive on and off; and an electronic circuit for adjusting the effective voltage ($U_{Mot}$) applied to the electric motor. In operation, a voltage supplied by the power supply declines with the discharge status of the power supply from a high-voltage range to a low-voltage range. During operation of the toothbrush in the high-voltage range (H), the effective voltage ($U_{Mot}$) applied to the electric motor is lowered to a level at which the electric motor has reached a rotational speed corresponding essentially to the rotational speed of the electric motor in the medium-voltage range.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

FIG. 3 depicts a schematic, cross sectional representation of an electric toothbrush according to one or more embodiments shown and described herein.

DETAILED DESCRIPTION OF THE INVENTION

Figure 1:
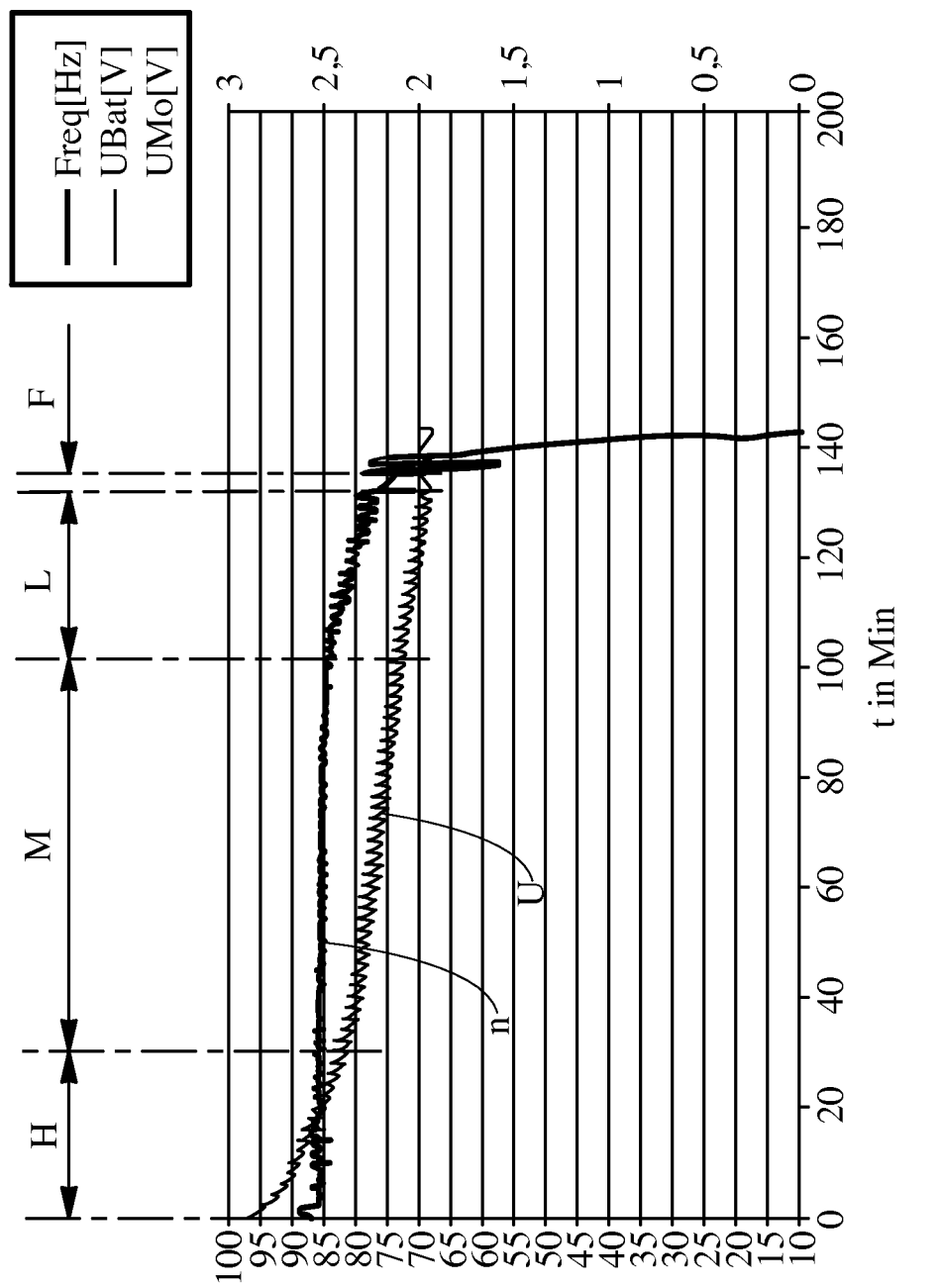
FIG. 1 is a graph depicting the rotational speed curve of an electric toothbrush with a voltage stabilizing circuit.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, an electric toothbrush is provided. The toothbrush includes a housing, a brush, an electric motor 4 for driving the brush, and a power supply for supplying the electric power required for operation of the toothbrush. In one embodiment, the voltage supplied by the power supply decreases with the discharge status of the power supply from a range H of high voltage to a range M of medium voltage and then to a range L of low voltage. The toothbrush also includes a switch mechanism for turning the drive on and off and an electronic circuit for adjusting the effective voltage Umot applied to the electric motor 4, such that during operation of the toothbrush in the high-voltage range H, the effective voltage Umot applied to the electric motor 4 is lowered to a level at which the electric motor 4 reaches a rotational speed which corresponds essentially to the rotational speed of the electric motor 4 in the medium-voltage range M, whereby the electric motor 4 is designed so that it still reaches a required minimum rotational speed in the range L of low allowed voltages.

In this way an electric toothbrush in which the power supply may be provided by batteries, accumulators or capacitors is made possible. By limiting the motor voltage to a moderate level, brush movements with a high dynamic that is perceived as unpleasant for the user are prevented. Furthermore in a phase with a high charge status of the power supply, excessive power consumption is prevented and the operating time at a moderate speed is prolonged on the basis of the savings thereby achieved. Furthermore it is possible to design the drive motor so that its optimum efficiency is at a voltage which is dominant over time during operation.

In one embodiment, the electronic circuit is implemented by an ASIC (Application-Specific Integrated Circuit). This ASIC preferably has a reset controller with a reference voltage source, which has temperature and voltage compensation, and a comparator. In one embodiment, an electronic switch, for example, a transistor, is triggered via the comparator output, thereby setting the effective motor voltage. The transistor is triggered, for example, by a pulse-width-modulated signal. The modulation frequency is high enough so that the electric motor consumes power based on the effective motor voltage (i.e., the voltage averaged over time) and the current flowing through the motor. In one embodiment, the motor is designed as a d.c. motor.

The electric toothbrush contains a permanently installed capacitor or has a battery receptacle into which can be inserted commercial 1.5 V primary batteries or 1.2 V secondary batteries, depending on the user's choice. For example, two such batteries may be inserted into the battery receptacle and connected in series. The voltage supplied by the power supply with new primary cells may then be in the range of 3 V and with fully charged accumulators in the range of 2.4 V. The electronic circuit is then designed to supply an effective voltage in the range of from about 1.8 V to about 2.3 V in which the intended rotational speed is reached when using commercial primary batteries as well as accumulators. The voltage capacity is designed so that tooth-brushing operations can be performed with a brushing time of approximately 2 minutes each with an average brush contact pressure. In one embodiment, the electric toothbrush has a rotating or oscillating and rotating brush head.

Figure 2:
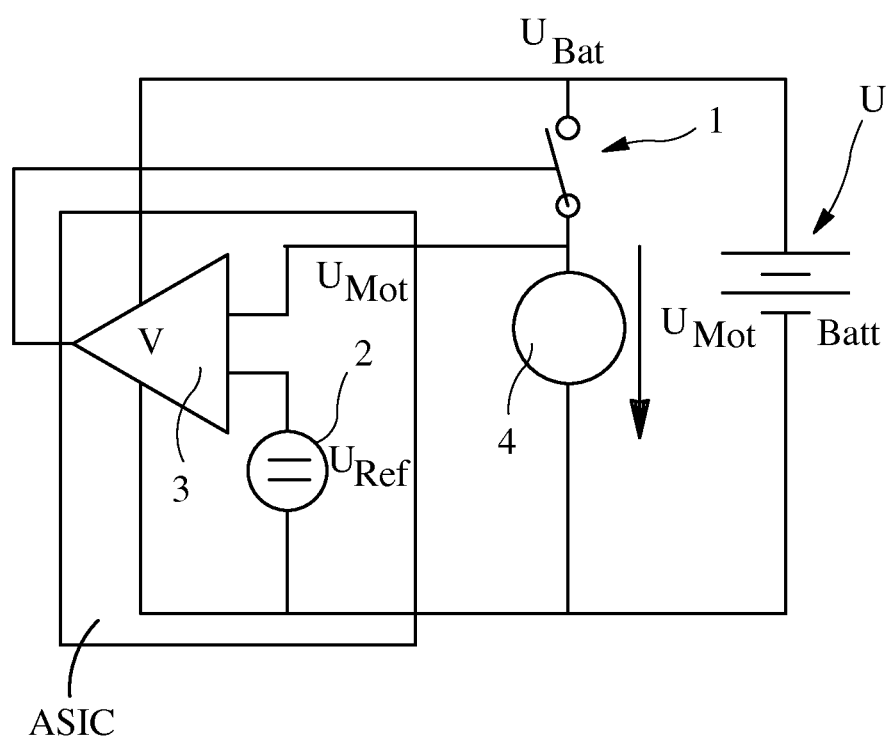
FIG. 2 is a circuit diagram of a voltage stabilizing circuit.

The diagram in FIG. 1 illustrates the relationship between an electric toothbrush power supply voltage U supplied by a battery and the rotational speed n of a motor 4 (see FIG. 2). The high voltage supplied by the voltage supply in the area H drops over a period of time due to spontaneous discharge and due to use of the electric toothbrush, dropping to an average voltage level of approximately 2.3 V prevailing in the area M. After withdrawing approximately 75% of the electric power stored in the voltage supply, the voltage in the area L drops further to a voltage in the range of approximately 2.1 V. In the area L, the example shown here, it is also connected to a short section F in which a tooth-brushing operation can be conducted with the lowest voltage that is still sufficient for the electric drive.

The electric toothbrush has an electronic circuit connected to the drive and the voltage supply, the circuit being designed to terminate operation of the toothbrush as soon as the power supply drops to inadmissibly low levels, so that in the event of use of accumulators, complete battery discharge is avoided. The electronic circuit may also be designed to comprise a voltage transformer circuit by means of which an increase in the voltage applied to the motor 2 to an adequate voltage is accomplished with a drop in the power supply below a predetermined voltage level. The electronic circuit is also designed to achieve a reduction in the effective voltage supplied to the motor when there is an especially high power supply voltage. At moderate power supply voltage levels and also during the final phase L, however, the motor 4 may also be operated with the voltage supplied by the power supply.

In order for the electronic circuit to be able to keep the rotational speed of the motor 4 as constant as possible, regardless of the charge state of the power supply, the motor 4 is designed so that it still reaches the desired rotational speed at the lowest feasible power supply voltage. In a variant with two batteries, this range is between about 1.8 V and about 2.3 V. During operation of the electric toothbrush in the high-voltage range H supplied on the part of the power supply as well as in the medium-voltage range M, the electric motor is operated in the range of its maximum efficiency. On depletion of the remaining approximately 25% of the energy stored by the power supply, there is only a slight discernable drop in the rotational speed of the electric toothbrush. In one embodiment, the electronic circuit is designed so that the rotational speed of the motor drops significantly only just before the battery is completely discharged and thereby signals the user the need for a battery replacement and/or recharging. This range between a significant drop in rotational speed and stoppage of the drive motor is of such dimensions that at least the tooth-cleaning operation of the current moment can still be concluded to satisfaction.

As shown in FIG. 2, an electronic circuit for operating the electric motor 4 in an electric toothbrush with which the typical drop in rotational speed over the lifetime of the battery is largely prevented. In one embodiment, the electronic circuit is implemented by an ASIC comprising essentially all the circuits required for implementation of voltage stabilization. For stabilization of rotational speed, the effective voltage $U_{Mot}$ on motor 4 is measured via a measurement device, optionally filtered and compared with a setpoint value. The power supply U is connected to the motor 4 via a switch mechanism 1 which is triggered by a high-frequency pulse-width-modulated signal, for example, such that when averaged over time, the rotational speed of the motor 4 and thus the frequency of movement of the driven brush carrier remains at an essentially constant level.

The electronic circuit can be implemented especially advantageously by a reset controller, comprising a reference voltage source 2, which has temperature and voltage compensation, and a comparator 3. The comparator compares the effective motor voltage $U_{Mot}$ with the voltage of the reference voltage source 2. If $U_{Mot}$ is greater than the voltage of the reference voltage source 2, then the switch mechanism 1 triggered by the output of the comparator 3 is opened. If the $U_{Mot}$ is lower than the voltage of the reference voltage source 2, then the switch mechanism 1 triggered by the output of the comparator 3 is closed. In one embodiment, the switch mechanism 1 is implemented by an electronic switch, for example, a transistor.

The electric toothbrush may be designed so that it comprises a structure component which comprises a receptacle space for the replaceable batteries or accumulators. The electronic circuit may be mounted on this structural component in such a way that the power supply may be designed as a preassembled module. The electronic circuit may be mounted on the structural component in such a way that it is protected from moisture or contaminants. It is also possible to implement the main device switch by means of the electronic circuit by the fact that an operating element mounted on the housing of the toothbrush in a manner that facilitates gripping by the user is connected to an input of the electronic circuit, which allows a corresponding switch signal to be supplied. The electronic circuit may also be provided with a charge status display, which displays the charge status of the power supply by means of optical or acoustic signals, for example.

Referring to FIG. 3, one embodiment of an electric toothbrush is shown. The electric toothbrush 10 may include a housing 12, an electric motor 4, a brush 14, a power supply 16, a switch mechanism 1 and an electronic circuit 18.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric toothbrush, comprising:
a housing;
a brush;
an electric motor for driving the brush;
a power supply for providing the electric power required for operation of the toothbrush, wherein a voltage supplied by the power supply declines with the discharge status of the power supply from a high-voltage range to a low-voltage range;
a switch mechanism for turning the drive on and off; and
an electronic circuit for adjusting the effective voltage ($U_{Mot}$) applied to the electric motor, such that during operation of the toothbrush in the high-voltage range (H), the effective voltage ($U_{Mot}$) applied to the electric motor is lowered to a level at which the electric motor has reached a rotational speed corresponding essentially to the rotational speed of the electric motor in the medium-voltage range,
wherein the electric motor is designed so that it still reaches a required minimum rotational speed in the range of low admissible voltages range; and wherein the effective voltage ($U_{Mot}$) on the electric motor is measured via a measurement device and compared with a setpoint value ($U_{Ref}$), the electronic circuit activating the voltage of the power supply when the effective voltage ($U_{Mot}$) drops below the setpoint value ($U_{Ref}$) and switches the effective voltage ($U_{Mot}$) off when the effective voltage ($U_{Mot}$) rises above the setpoint value ($U_{Ref}$).

2. The electric toothbrush according to claim 1, wherein the electric circuit is arranged to filter the effective voltage ($U_{Mot}$) prior to comparing the effective voltage ($U_{Mot}$) with the setpoint value ($U_{Ref}$).

3. The electric toothbrush according to claim 1, wherein the motor achieves its maximum efficiency at a voltage in the range of a medium-voltage level.

4. The electric toothbrush according to claim 1, wherein the electronic circuit has a reset controller.

5. The electric toothbrush according to claim 4, wherein the reset controller comprises a temperature and voltage compensated reference voltage source and a comparator.

6. The electric toothbrush according to claim 5, wherein the effective voltage ($U_{Mot}$) is adjusted via an output of the comparator.

7. The electric toothbrush according to claim 1, wherein the power supply includes at least one primary or secondary battery or a capacitor.

8. The electric toothbrush according to claim 1, wherein the electronic circuit is designed so that the rotational speed provided for operation in the medium-voltage range is reached when using either primary or secondary batteries.

9. The electric toothbrush according to claim 1, wherein the drive is designed so that the brush executes a rotating or an oscillating and rotating movement.

\* \* \* \* \*